(12) United States Patent
Tsai et al.

(10) Patent No.: US 9,339,572 B2
(45) Date of Patent: May 17, 2016

(54) METHODS AND SOLUTIONS FOR KILLING OR DEACTIVATING SPORES

(71) Applicant: EP Technologies LLC, Akron, OH (US)

(72) Inventors: Tsung-Chan Tsai, Cuyahoga Falls, OH (US); Sameer Kalghatgi, Fairlawn, OH (US); Daphne Pappas Antonakas, Hudson, OH (US); Robert L. Gray, Hudson, OH (US)

(73) Assignee: EP Technologies LLC, Akron, OH (US)

(*) Notice: Subject to any disclaimer, the term of this patent is extended or adjusted under 35 U.S.C. 154(b) by 385 days.

(21) Appl. No.: 13/843,189

(22) Filed: Mar. 15, 2013

(65) Prior Publication Data

US 2015/0265736 A1    Sep. 24, 2015

(51) Int. Cl.
| | |
|---|---|
| *A61L 2/00* | (2006.01) |
| *B01J 19/08* | (2006.01) |
| *B08B 3/00* | (2006.01) |
| *G01N 23/00* | (2006.01) |
| *A61L 2/14* | (2006.01) |
| *A01N 59/00* | (2006.01) |
| *A01N 31/00* | (2006.01) |

(Continued)

(52) U.S. Cl.
CPC . *A61L 2/14* (2013.01); *A01N 31/00* (2013.01); *A01N 59/00* (2013.01); *A01N 61/00* (2013.01); *A61L 2/0011* (2013.01); *A61L 2/0088* (2013.01); *A61L 2/18* (2013.01)

(58) Field of Classification Search
CPC .............. A61L 2/00; B01J 19/08; A01N 1/00; C23F 11/00
USPC ........................... 422/22–23, 186.04, 186.05; 250/455.11; 134/26
See application file for complete search history.

(56) References Cited

U.S. PATENT DOCUMENTS

| | | | |
|---|---|---|---|
| 3,918,987 A | 11/1975 | Kopfer | |
| 4,020,856 A | 5/1977 | Masterson | |

(Continued)

FOREIGN PATENT DOCUMENTS

| | | |
|---|---|---|
| WO | 0110215 | 2/2001 |
| WO | 02059046 | 8/2002 |

(Continued)

OTHER PUBLICATIONS

Klimpel, Kurt, M.D. "Clostridium difficle Test Exposure to BIT Plasma"; Plasma Clostridium difficile Killing Trials; 2009; 5 pages.

(Continued)

*Primary Examiner* — Monzer R Chorbaji
(74) *Attorney, Agent, or Firm* — Calfee, Halter & Griswold LLP (57) ABSTRACT

Exemplary methods and systems for killing or deactivating spores include applying a fluid to a surface containing a spore; and applying direct or indirect plasma to the surface for a period of time. In some embodiments, the fluid includes water. In some embodiments, the spore is *Clostridium difficile* and in some is *Bacillus Anthracis*. In some embodiments, the fluid is in the form of a mist and in some is in the form of a vapor. In some embodiments, peroxynitrite is created in the fluid during the method. Another exemplary embodiment of killing or deactivating a spore includes treating spores with direct plasma or an indirect plasma for a period of time and applying an antimicrobial to the spores. In some embodiments, the antimicrobial is an alcohol, a bleach or an alcohol-based sanitizer.

30 Claims, 4 Drawing Sheets

(51) Int. Cl.
*A01N 61/00* (2006.01)
*A61L 2/18* (2006.01)

(56) References Cited

U.S. PATENT DOCUMENTS

| | | | |
|---|---|---|---|
| 5,876,663 | A | 3/1999 | Laroussi |
| 6,030,506 | A | 2/2000 | Bittenson et al. |
| 6,176,941 | B1 | 1/2001 | Jewett et al. |
| 6,387,238 | B1 | 5/2002 | Merk et al. |
| 6,706,243 | B1 | 3/2004 | Sias et al. |
| 6,723,091 | B2 | 4/2004 | Goble et al. |
| 6,911,225 | B2 | 6/2005 | Ruan et al. |
| 7,004,356 | B1 | 2/2006 | Sayers |
| 7,008,592 | B2 | 3/2006 | Sias et al. |
| 7,163,664 | B2 | 1/2007 | Paskalov et al. |
| 7,291,314 | B2 | 11/2007 | Paskalov et al. |
| 7,326,382 | B2 | 2/2008 | Adiga et al. |
| 7,569,203 | B2 | 8/2009 | Fridman et al. |
| 7,608,839 | B2 | 10/2009 | Coulombe et al. |
| 7,829,051 | B2 | 11/2010 | Fridman et al. |
| 7,989,673 | B2 | 8/2011 | Paskalov et al. |
| 8,048,930 | B2 | 11/2011 | Bobbert |
| 8,354,057 | B2 | 1/2013 | Heselton et al. |
| 8,383,036 | B2 | 2/2013 | Sloan et al. |
| 8,388,618 | B2 | 3/2013 | Fridman et al. |
| 2004/0120844 | A1* | 6/2004 | Tribelsky et al. ............ 422/2 |
| 2004/0216845 | A1 | 11/2004 | Golkowski |
| 2006/0189976 | A1 | 8/2006 | Karni et al. |
| 2006/0223729 | A1 | 10/2006 | Hamblin et al. |
| 2006/0229225 | A1 | 10/2006 | Martin |
| 2007/0251953 | A1 | 11/2007 | Criswell et al. |
| 2009/0041617 | A1 | 2/2009 | Lee |
| 2009/0054896 | A1 | 2/2009 | Fridman et al. |
| 2009/0175956 | A1 | 7/2009 | Buschmann et al. |
| 2010/0145253 | A1 | 6/2010 | Gutsol et al. |
| 2010/0168499 | A1 | 7/2010 | Gutsol et al. |
| 2010/0196505 | A1 | 8/2010 | Kaiser et al. |
| 2010/0209293 | A1 | 8/2010 | Ikawa et al. |
| 2010/0280513 | A1 | 11/2010 | Juergen et al. |
| 2010/0296977 | A1 | 11/2010 | Hancock |
| 2011/0112528 | A1 | 5/2011 | Stieber et al. |
| 2011/0171188 | A1 | 7/2011 | Morfill et al. |
| 2011/0251604 | A1 | 10/2011 | Staack et al. |
| 2012/0039747 | A1 | 2/2012 | Morfill et al. |
| 2012/0100037 | A1 | 4/2012 | Shannon et al. |
| 2012/0305787 | A1 | 12/2012 | Henson |

FOREIGN PATENT DOCUMENTS

| | | |
|---|---|---|
| WO | 2006076334 | 7/2006 |
| WO | 2006116252 | 11/2006 |
| WO | 2007048806 | 5/2007 |
| WO | 2007063987 | 6/2007 |
| WO | 2010009103 | 1/2010 |
| WO | 2010022160 | 2/2010 |
| WO | 2010107722 | 9/2010 |
| WO | 2010107741 | 9/2010 |
| WO | 2010107744 | 9/2010 |
| WO | 2010107745 | 9/2010 |
| WO | 2010107746 | 9/2010 |
| WO | 2012018891 | 2/2012 |

OTHER PUBLICATIONS

Venezia, Richard, et al., "Lethal Activity of Nonthermal Plasma . . . ", Univ. of Chicago Press, Infection Control and Hospital Epidemiology, vol. 29, No. 5, May 2008, http://www.jstor.org/stable/10.1086/588003.

Lawley, Trevor, D., et al., "Proteomic and Genomic Characterization of Highly Infectious . . . ", J. Bacteriol. 2009, vol. 191, No. 17, pp. 5377-5386, Jun. 2009, http://jb.asm.org/content/191/1715377.

Oehmigen, K., et al., "The Role of Acidification for Antimicrobial . . . ", Wiley InterScience, Plasma Process. and Polym. 2010, 7, pp. 250-257, 2010.

Lawley, Trevor, D., et al., "Use of Purified Clostridium difficile Spores . . . ", Appl. Environ. Microbiol., pp. 6895-6900, Aug. 2010.

Ermolaeva, Svetlana, A., et al., "Bactericidal effects of non-thermal argon plasma . . . ", J. Med. Microbiol., Sep. 2010, http://jmm.sgmjournals.org/content/60/1/75.full.

Traylor, Matthew, J., et al., "Long-term antibacterial efficacy of air plasma-activated water", J. Phys. D: Appl. Phys., Nov. 2011, http://www.stacks.iop.org/JPhysD/44/472001.

Huang, Yaohua, "Non-thermal Plasma Inactivation of Bacillus Amyloliquefaciens Spores", Master's Thesis, Univ. of Tennessee, 2011, http://www.trace.tennessee.edu/utk_gradthes/980.

Tolls, Elisabeth, H., et al., Surface Layers of Clostridium difficile Endospores, J. Bacteriol. 2011, vol. 193, No. 23, pp. 6461-6470, 2011.

Paredes-Sabja, D., et al., "Adherence of Clostridium difficile spores to Caco-2 cells in culture", J. Med. Microbiol., pp. 1208-1218, 2012.

Pei., X., et al., "Inactivation of a 25.5 . . . Enterococcus faecalis biofilm . . . ", J. Phys. D: Appl. Phys., http://www.stacks.iop.org/JPhysD/45/165205, Apr. 2012.

Escobar-Cortes, K., et al., "Proteases and sonication specifically remove the exosporium layer . . . ", J. Microbiol. Methods, Jan. 2013.

International Search Report and Written Opinion from International Application No. PCT/US2013/063360, date of mailing Dec. 11, 2013.

Burlica et al. "Formation of H2 and H2O2 in a Water-Spray Gliding Arc Nonthermal Plasma Reactor", Industrial & Engineering Chemistry Research, vol. 49, No. 14, Jun. 24, 2010.

International Search Report and Written Opinion from International Application No. PCT/US2014/030361, date of mailing Jul. 16, 2014.

* cited by examiner

METHODS AND SOLUTIONS FOR KILLING OR DEACTIVATING SPORES

TECHNICAL FIELD

The present invention relates generally to methods and solutions for fast killing or deactivating spores.

BACKGROUND OF THE INVENTION

Spore formation is a sophisticated mechanism by which some Gram positive bacteria survive conditions of external stress and nutrient deprivation by producing a multi-layered protective capsule enclosing their dehydrated and condensed genomic DNA. When such bacterial spores encounter a favorable environment, germination can take place enabling the bacteria to reproduce, and, in the case of pathogenic species, cause disease. Bacterial spores possess a coat and membrane structure that is highly impermeable to most molecules that could be toxic to the dormant bacteria. Therefore, spores are highly resistant to damage by heat, radiation, and many of the commonly employed anti-bacterial agents, and generally can only be destroyed by some severe chemical procedures including oxidizing vapors such as hydrogen peroxide, chlorine dioxide and ozone.

People receiving medical care can acquire serious infections called healthcare-associated infections (HAIs). While most types of HAIs are declining, one—caused by the germ *Clostridium difficile*, "*C. difficile*"—remains at historically high levels. *C. difficile* is linked to 14,000 American deaths each year. Those most at risk are people, especially older adults, who take antibiotics and also receive long term medical care.

*C. difficile* is an anaerobic, Gram positive bacterium. Normally fastidious in its vegetative state, it is capable of sporulating when environmental conditions no longer support its continued growth. The capacity to form spores enables the organism to persist in the environment (e.g., in soil and on dry surfaces) for extended periods of time.

Current methods of killing or deactivating *C. difficile* include applying bleach, liquid solutions containing hydrogen peroxide, and other biocidal compounds, and/or ultraviolet radiation (UV) to *C. difficile* for a period of time longer than 3 minutes.

Anthrax spores, *Bacillus anthracis* ("*B. anthracis*") is the pathogenic organism that causes anthrax. Anthrax is a disease that is frequently fatal due to the ability of this bacterium to produce deadly toxins. *B. anthracis* also forms spores. Inhalation of anthrax spores is frequently fatal, particularly if treatment is not started prior to the development of symptoms.

Anthrax spores are also among the most difficult spores to kill or deactivate. Present methods of killing or deactivating anthrax spores use of pressurized steam at elevated temperatures, topical treatment with highly caustic concentrated sodium hypochlorite solutions or with certain disinfecting foam products.

One of the reasons it is very difficult to kill or deactivate dry spores is due to their tendency to aggregate and form multi-layered structures. In addition, the dry spores adhere to surfaces and skin very strongly, making it very difficult to physically remove them.

SUMMARY

Exemplary methods and systems for killing or deactivating spores include applying a fluid to a surface containing a spore; and applying direct plasma to the surface for a period of time.

Additional exemplary methods and systems for killing or deactivating spores include applying a fluid to a surface containing a spore; and applying indirect plasma to the surface for a period of time.

In some embodiments, the fluid includes water. In some embodiments, the spore is *Clostridium difficile* and in some it is *Bacillus anthracis*. In some embodiments, the fluid is in the form of a mist and in some it is in the form of a vapor. In some embodiments, peroxynitrite is created in the fluid during the method. In some embodiments, peroxyacetic acid and several other oxygen and nitrogen derivatives are created in the fluid during the method.

Another exemplary embodiment of killing or deactivating a spore includes treating spores with direct plasma or indirect plasma for a period of time and applying an antimicrobial to the spores. In some embodiments, the antimicrobial is an alcohol, a bleach or alcohol based sanitizer.

BRIEF DESCRIPTION OF THE DRAWINGS

These and other features and advantages of the present invention will become better understood with regard to the following description and accompanying drawings in which.

DETAILED DESCRIPTION

Plasmas, or ionized gases, have one or more free electrons that are not bound to an atom or molecule. Plasmas may be generated using a variety of gases including, air, nitrogen, noble gases (He, Ar, Xe, Kr, etc), oxygen, carbon dioxide and mixtures thereof under an electric field. In addition, non-thermal plasmas provide high concentrations of energetic and chemically active species. They can operate far from thermodynamic equilibrium with high concentrations of active species and yet remain at a temperature that is substantially the same as room temperature. The energy from the free electrons may be transferred to additional plasma components creating additional ionization, excitation and/or dissociation. Fluid that is contacted with plasma becomes "activated" and is referred to herein as plasma activated fluid, and in some embodiments, the plasma activated fluid is plasma activated water.

In some embodiments, plasmas may contain superoxide anions $[O2^-]$, which react with $H^+$ in acidic media to form hydroperoxy radicals, $HOO^-$ $[O_2^-]+[H^+]\rightarrow[HOO^-]$. Other radical species may include $OH^-$ and $NO^-$ in aqueous phase or the presence of air or gas. Treating water with plasma results in plasma activated water that may contain concentrations of one or more of ozone, $H_2O_2$, nitrates, nitrites, radicals and other active species.

Activating water with plasma to obtain plasma activated water is shown and described in co-pending U.S. Provisional Application Ser. No. 61/621,078 titled Sanitization Station Using Plasma Activated Fluid, filed on Apr. 6, 2012 and co-pending U.S. Provisional Application Ser. No. 61/710,263 titled Solutions and Methods of Making Solutions to Kill or Deactivate Spores Microorganisms, Bacteria and Fungus, filed on Oct. 5, 2012. Both of which are incorporated by reference herein in their entirety. Several other patents and applications such as: PCT Application Nos. WO 02/059046, titled Method of Activation of Chemically Pure and Potable Water and filed on Jan. 25, 2002; WO 2007/048806, titled Method for the Preparation of Biocidal Activated Water Solutions and filed Oct. 25, 2006; WO 2012/018891, which is titled Materials for Disinfection Produced by Non-Thermal Plasma and was filed on Aug. 3, 2011; and U.S. Pat. No. 7,291,314, titled Activated Water Apparatus and Methods and filed Dec. 20, 2001, are incorporated herein by reference in their entirety for their disclosure on activating fluid.

Figure 1:
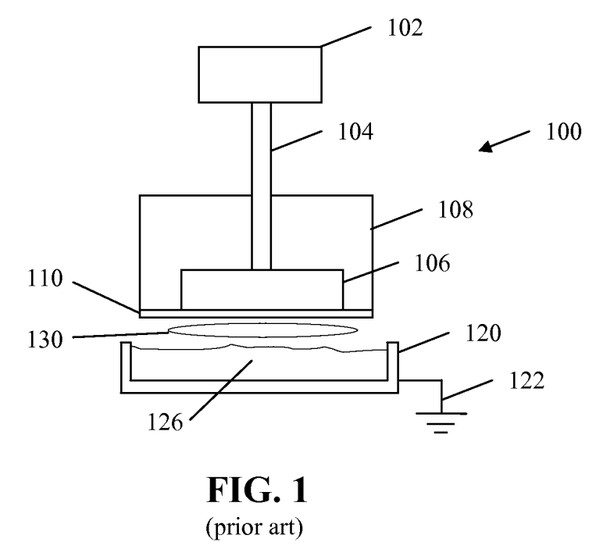
FIG. 1 illustrates a prior art embodiment for creating activated water using direct plasma.

It is known to treat water and other fluids with plasma to "activate" them. One method of activating water and other liquids is illustrated in FIG. 1, which is a prior art dielectric barrier discharge ("DBD") plasma generating system 100. The prior art plasma generating system 100 includes a high voltage source 102, a conductor 104, a housing 108, a high voltage electrode 106 and a dielectric barrier 110. The plasma generating system 100 also includes a container 120 which is grounded with grounding conductor 122. During operation, the high voltage source 102 is turned on and plasma 130 forms below the dielectric barrier 110. High voltage power source 102 may be a DC power source, a high frequency AC power source, an RF power source, a pulsed DC power source, a pulsed AC power source, a microwave power source or the like. The power supply can be pulsed with a duty cycle of 0-100% and pulse duration of 1 nanosecond up to 1 microsecond.

The plasma contacts the water or fluid 126 and activates the water or fluid 126. Fluid 126 activated by direct contact with plasma is referred to herein as "direct plasma activated fluid."

Figure 2:
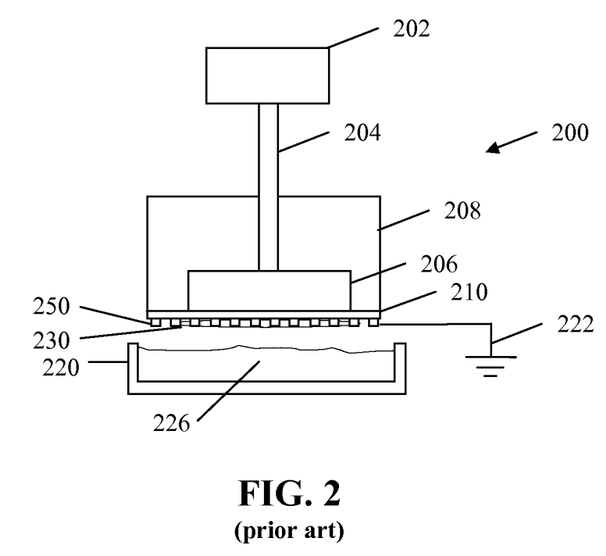
FIG. 2 illustrates a prior art embodiment for creating activated water using indirect plasma.

FIG. 2 illustrates an exemplary prior art system 200 for activating a fluid using indirect plasma. System 200 includes a high voltage power source 202. High voltage power source 202 may be a DC power source, a high frequency AC power source, an RF power source, a microwave power source, a pulsed DC power source, a pulsed AC power source or the like. The power supply can be pulsed with a duty cycle of 0-100% and pulse duration of 1 nanosecond up to 1 microsecond.

The exemplary system 200 includes a DBD plasma generator 208 connected to high voltage power source 202 by cable 204. Direct DBD plasma generator 208 includes a high voltage electrode 206 and a dielectric barrier 210 located between high voltage electrode 206 and the fluid 226 that is to be activated. A filter 250 is also included. Filter 250 is a conductive mesh that is grounded by grounding conductor 222.

During operation of system 200, when high voltage electrode 206 is energized, plasma 230 forms below the dielectric barrier 210, and the filter 250 (if the filter 250 is made of a conductive material and grounded) prevents charged ions and electrons from passing through and contacting the fluid 226 to be activated. Thus, only neutral species pass through and activate the fluid 226. This is typically referred to as "afterglow" or "indirect" plasma. In some embodiments, the fluid is water. Fluid 226 activated by afterglow that passes through, or is created through filter 250, is referred to "indirect plasma activated fluid."

Figure 3:
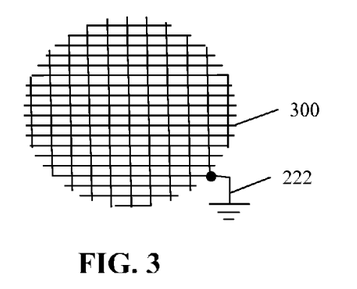
FIG. 3 illustrates an exemplary mesh filter for use in the exemplary embodiment of FIG. 2.

The experimental data provided below generated by indirect plasma, utilized a copper mesh as a filter. FIG. 3 illustrates the exemplary copper mesh 300 that was utilized as filter 250. The copper mesh was a copper woven wire having a 16×16 mesh with a 0.011" wire diameter and a 0.052" opening size (67% opening area). A mesh with different conducting materials, wire diameters and opening sizes may be used.

In the exemplary embodiments disclosed herein the fluid may be water. In some embodiments, the properties of the fluid may be altered prior to activation by plasma or indirect plasma to increase or decrease concentration of species, radicals and the like. For example, the pH of water may be adjusted to be acidic or basic. The pH may be adjusted by, for example, adding acid to the water prior to activation. The pH level may be lowered through the activation process. In one embodiment, the pH level of the activated water is about 2.0, in another the pH is between about 2.0 and 3.5, and in yet another is about 2.7. Still, in another the pH is less than about 3.0 and in another embodiment is less than about 2.0. In one embodiment, the pH is about 2.0.

In addition, the properties of the activated fluid may be adjusted during the activation process itself by altering the gas that is ionized at the electrode. For example, the gas that is ionized may be normal air, $N_2$, $O_2$, He, Ar, Xe, Kr, combinations thereof at various ratios, or the like. In some embodiments, one or more inert gases are used in the plasma generating process. In some embodiments, one or more noble gases are used in the plasma generating process, and in some embodiments, combinations of noble and other gases are used in the plasma generating process.

Further, additives may be added before or after the fluid is activated to increase efficacy or stabilization of the resulting solution. Other additives that may be used depending on the desired results include, for example, alcohol, silver salts, e.g., silver nitrate or silver chloride, or colloidal silver; zinc salts, e.g. zinc chloride, zinc lactate, or zinc oxide; suspensions containing metal nanoparticles; chlorhexidine; anionic, cationic, non-ionic and/or amphoteric surfactants; emulsifiers; hydrotropes; glycerol; chelating agents; alcohols; quaternary ammonium compounds, acids (organic or inorganic); bases; or surface tension decreasing agents.

Fluid 226 may be a source of water, or of water with additional additives. In one embodiment, the fluid is tap water, however, the water may be distilled water, deionized water, tap water, filtered water, saline, water with acidic properties, water with basic properties or water mixed with additives such as, for example, alcohol. In addition, other additives may be used to optimize generation or increase performance and/or increase stability. These additives may include, for example chelators to reduce metal degradation; surfactants to improve penetration of the solution, to reduce the impact of organic load and/or buffers used to adjust the pH. In addition, in some embodiments corrosion inhibitors may be added, such as, for example, inorganic sulfates, inorganic phosphates. In some embodiments, a zeolite buffering system may be used. In some embodiments, one or more of these additives are added prior to activation of the water.

Figure 4:
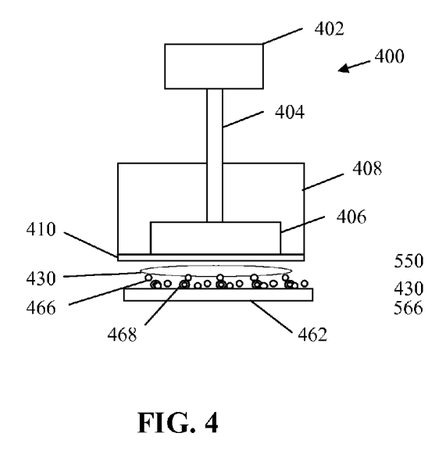
FIGS. 4 and 4A illustrate an exemplary system and method for killing or deactivating spores.

FIG. 4 illustrates an exemplary embodiment of a system 400 for killing or deactivating spores 468 on a surface 462. The spore may be, for example, *Clostridium difficile* "C. diff," *Bacillus anthracis* "Anthrax" or other spores. The spores are dry spores, and in some cases, layers of dried spores. The surface may be any surface, including for example, surfaces in a hospital or nursing home like stainless steel, glass, ceramic, linens, curtains, rubber, fabric or plastics. In some embodiments, the surface may be skin or tissue.

The system 400 includes a high voltage source 402 connected to an electrode 406 by cable 404, a dielectric barrier 410 and a housing 408. System 400 is used to kill or deactivate spores 468 that have been misted by droplets or vapor 466. The operating methodology is described with respect to FIG. 4A below.

Figure 4A:
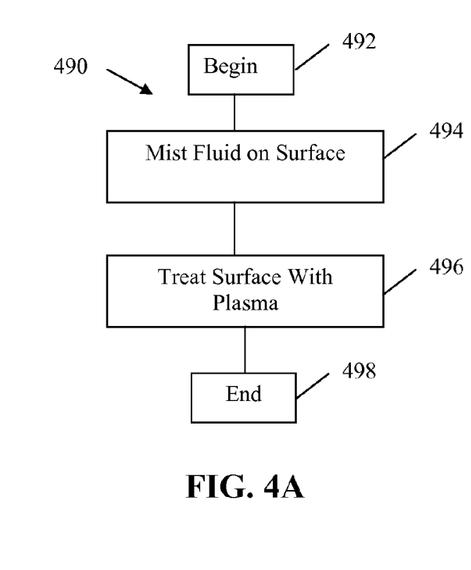

FIG. 4A illustrates an exemplary methodology 490 for killing a spore using direct plasma. The methodology begins at block 492. At block 494 fluid is placed on a dry surface containing spores to be treated. In some embodiments, the fluid is in a mist or droplet form. The droplet or mist size can vary and in some embodiments is between about 50 micrometers and 3 millimeters in diameter. In some embodiments the diameter size is less than about 1 millimeter, in some embodiments is less than about 500 micrometers, and in some embodiments is less than about 250 micrometers, and in some embodiments is less than about 100 micrometers. The volume of the droplet or mist can vary and is between about 0.1 microliter to 500 microliters. In some embodiments the volume of the droplets or mist is less than about 250 microliters. In some embodiments, the droplets or mist is less than about 100 microliters, and in some embodiments the droplets or mist is less than about 10 microliters. In some embodiments, the mist is a vapor. In some embodiments, the fluid is water. In some embodiments, the mist is a vapor. In some embodiments, the fluid is water. In some embodiments, the mist of fluid covers the top layer of spores. In some embodiment, the mist of fluid covers only a portion of the spores. In some embodiments, the fluid is water with one or more of the additives identified above. In some embodiments, the pH of the fluid is adjusted prior to misting the fluid.

The surface may be any surface, such as, for example, table, a bed, etc. made of polymer, metal, rubber, glass, silicone, fabric material or the like. The surface may be a hard surface or a soft surface, such as, for example, linens, curtains and the like. In addition, the surface may be tissue or skin. After the surface has been misted with a fluid or vapor, the surface is treated with direct plasma at block 496. The direct plasma may be generated from air, nitrogen, an inert gas, a noble gas or any combinations thereof as described above.

Treatment time may vary depending on the surface. In some embodiments, the surface is treated for about 5 minutes. In some embodiments, the surface is treated for less than about 5 minutes. In some embodiments, the surface is treated for less than about 3 minutes. In some embodiments, the surface is treated for less than about 1 minute. In some embodiments, the surface is treated for about 30 seconds or less. In some embodiments, the surface is treated for more than about 5 minutes. After the surface has been treated, the methodology ends at block 498.

Treating the surface activates the fluid or water which penetrates the shell of the spore and kills or deactivates the spores. In some embodiments, the plasma contacts the spores directly between droplets or vapor and creates an opening for the activated fluid to penetrate the shell of the spore to kill or deactivate the spore.

In some embodiments, the methodology 490 generates peroxynitrite which has a half life of around 1 second. The misted fluid has a relatively large surface area compared with non-misted fluid in container, and the large surface area allows the plasma to activate the misted fluid quickly and more effectively, as higher concentrations of reactive oxygen and nitrogen species such as ozone, hydrogen peroxide, nitrites and nitrates are generated. It also allows the generation of peroxynitrite which almost immediately contacts the spore surface, as opposed to having to migrate through a larger volume of water to make contact with the spores. Thus, the peroxynitrite may contact the spore prior to its degeneration.

Figure 5:
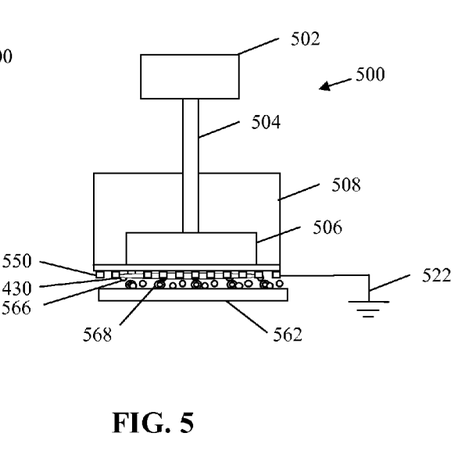
FIGS. 5 and 5A illustrate an exemplary system and method for killing or deactivating spores.

FIG. 5 illustrates an exemplary embodiment of a system 500 for killing or deactivating spores 568 on a surface 562. The spores are dry spores, and in some cases are layers of dry spores. The spore may be, for example, *C. difficile*, anthrax or other spores. The system 500 includes a high voltage source 502 connected to an electrode 506 by cable 504, a dielectric barrier 510, a housing 508 and a filter 550. System 500 is used to kill or deactivate spores 568 that have been misted by droplets or vapor 566. The operating methodology is described with respect to FIG. 5A below.

Figure 5A:
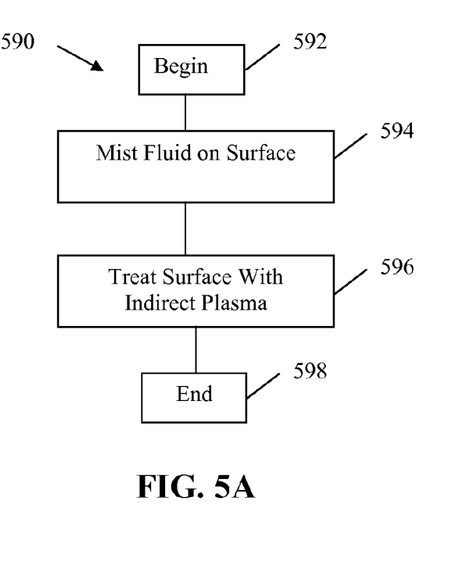

FIG. 5A illustrates an exemplary methodology 590 for killing a spore using indirect plasma. The methodology begins at block 592. At block 594 fluid is misted on the surface to be treated. In some embodiments, the fluid is in a mist or droplet form. The droplet or mist size can vary and is between about 50 micrometers and 3 millimeters. In some embodiments the size is less than about 1 millimeter, in some embodiments is less than about 500 micrometers, and in some embodiments is less than about 250 micrometers, and in some embodiments is less than about 100 micrometers. The volume of the droplet or mist can vary and is between about 0.1 microliter to 500 microliters. In some embodiments the volume of the droplets or mist is less than about 250 microliters. In some embodiments, the droplets or mist is less than about 100 microliters, and in some embodiments the droplets or mist is less than about 10 microliters. In some embodiments, the mist is a vapor. In some embodiments, the fluid is water. In some embodiments, the mist of fluid covers the top layer of spores. In some embodiment, the mist of fluid covers only a portion of the spores. In some embodiments, the fluid is water with one or more of the additives identified above. In some embodiments, the pH of the fluid is adjusted prior to misting the fluid.

The surface may be any surface as described above with respect to FIGS. 4 and 4A. After the surface has been misted with a fluid, the surface is treated with indirect plasma at block 596. The indirect plasma may be generated from air, nitrogen, a reactive gas, a noble gas or any combinations thereof as described above.

Treatment time may vary depending on the surface. In some embodiments, the surface is treated for about 5 minutes. In some embodiments, the surface is treated for less than about 5 minutes. In some embodiments, the surface if treated for less than about 3 minutes. In some embodiments, the surface is treated for less than about 1 minute, and in some embodiments less than about 30 seconds. In some embodiments, the surface is treated for more than about 5 minutes. After the surface has been treated, the methodology ends at block 598.

Treating the surface activates the fluid which penetrates the shell of the spore and kills or deactivates the spores. In some embodiments, the indirect plasma or afterglow contacts the spores directly between fluid droplets or fluid vapor and creates an opening for the activated fluid to penetrate the shell of the spore to kill or deactivate the spore.

In some embodiments, the methodology 590 generates peroxynitrite which has a half life of around 1 second. The misted fluid has a relatively large surface area compared with fluid in container, and the large surface area allows the indirect plasma or afterglow to activate the misted fluid quickly and more effectively, as higher concentrations of reactive oxygen and nitrogen species such as ozone, hydrogen peroxide, nitrites and nitrates are generated. It also allows the peroxynitrite to almost immediately contact the spore surface, as opposed to having to migrate through a larger volume of water to make contact with the spores. Thus, the peroxynitrite may contact the spores before it degenerates.

Figure 6:
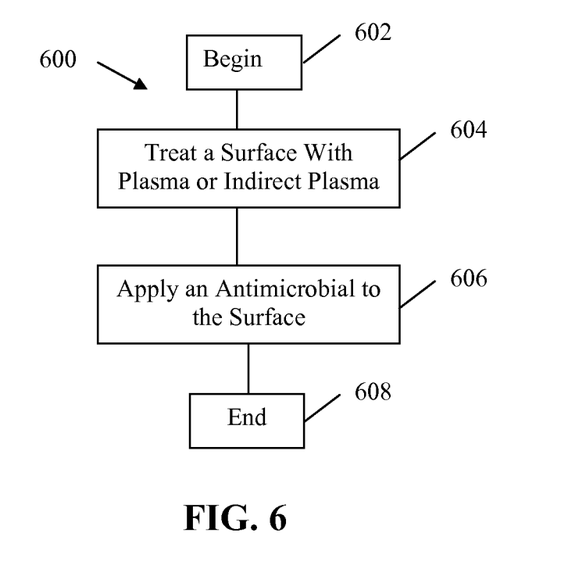
FIG. 6 illustrates another exemplary methodology for killing or deactivating spores.

FIG. 6 illustrates another exemplary methodology for killing or deactivating spores. The methodology begins at block 602. At block 604 a surface is exposed to plasma. The surface may be treated with indirect plasma or direct plasma. The treatment time may be for about 1 minute. The treatment time may be less than about 1 minute. The treatment time may be between about 1 minute and 3 minutes. In some embodiments, the treatment time is about 5 minutes. Still in some embodiments, the treatment time is between about 3 and 5 minutes, and in some embodiments, the treatment time is more than about 5 minutes.

After the treatment has ended, an antimicrobial is applied to the surface. The antimicrobial may be for example, alcohol based sanitizer; alcohol; bleach; silver salts, e.g., silver nitrate or silver chloride, or colloidal silver; zinc salts, e.g. zinc chloride, zinc lactate, or zinc oxide; suspensions containing metal nanoparticles; chlorhexidine; anionic, cationic, non-ionic and/or amphoteric surfactants; emulsifiers; hydrotopes; glycerol; chelating agents; quatenary ammonium compounds, acids (organic or inorganic); bases; or surface tension decreasing agents; or the like. In some embodiments, the antimicrobial may be applied to the surface prior to treating the surface with direct or indirect plasma. The methodology ends at block 608.

In some embodiments, the prior art filter 250 may be replaced by a filter having a carulite catalyst to filter out ozone. Other materials and/or coatings may be used to block certain species in the plasma from passing through to the fluid. In some embodiments, multiple filters are utilized, thus a copper filter could be used to filter out charged particles and a second carulite coated mesh could be used to filter out ozone. In addition, a wire mesh may be used for electromagnetic shielding. In some embodiments, the filter is conductive and is used to tune the electric field between the plasma generator and conductive filter to control the density and/or concentrations of reactive species that pass through the filter.

Experimental Results

An alternating polarity pulsed power supply was used in the experiment to generate plasma. The pulse frequency was 3.5 kHz and the pulse duration was 10 μs. The amplitude of the voltage pulse was 20 kV peak to peak with a 5 V/ns rise time. The gap distance between the plasma generating system and the treated surface was about 1 to 2 mm. The experiments used air as the plasma working gas under the pressure of 1 atmosphere, which is the ambient pressure.

Experimental results demonstrated the ability to kill or deactivate *C. diff.* with the exemplary systems and methodologies described herein. In one case, deactivation was observed after only 30 seconds of exposure to plasma.

*C. diff* spores were applied on stainless steel coupons and microscope slide surfaces. A volume of 10 μl of *C. diff* spores ($10^8$ CFU/ml) in sterile water was added onto the sterile surfaces and left to dry for 30 min. Then the contaminated surfaces were exposed to plasma as described below. After treatment, the coupons and slides were placed in test tubes filled with neutralizer (9.9 ml). The test tubes were sonicated for 1 minute and vortexed for 15 seconds to fully remove the spores from the surfaces. The neutralizer solution containing spores was diluted and plated on Brain Heart Infusion Agar supplemented with 0.1% Sodium Taurocholate (BHIT). Anaerobic 36-48-hr incubation was then performed at 37° C., followed by the estimation of colony forming units (CFU).

In one experiment, *C. difficile* was placed on stainless steel coupons and allowed to dry for about 30 minutes. As illustrated in the chart below, a first stainless steel coupon with the *C. difficile* was treated with indirect plasma for a 1 minute period of time resulting in a log reduction of 0.43 colony forming units per milliliter (CFU/ml). A second stainless steel coupon with *C. difficile* was treated with indirect plasma for 5 minutes resulting in a 0.63 CFU/ml. Next, another stainless steel coupon with *C. difficile* was treated with direct plasma for a 1 minute period of time resulting in a log reduction of 0.45 CFU/ml. In addition, a fourth stainless steel coupon with *C. difficile* was treated with direct plasma for 5 minutes resulting in a log reduction of 1.11 CFU/ml. These test results, demonstrate that while plasma and indirect plasma alone will kill or deactivate some spores, plasma and indirect plasma alone do not provide the best results.

| Plasma Type | Treatment Time | Fluid Mist | Log Reduction (CFU/ml) | Surface |
|---|---|---|---|---|
| Indirect | 1 min | No | 0.43 | Stainless Steel |
| Indirect | 5 min | No | 0.63 | Stainless Steel |
| Direct | 1 min | No | 0.45 | Stainless Steel |
| Direct | 5 min | No | 1.11 | Stainless Steel |

Next, as illustrated in the chart below, a stainless steel coupon with *C. difficile* was misted with water and treated with direct plasma for a 30 second, 1 minute or 3 minute period of time, each of which resulted in a log reduction of 3.43, 4.48 and 4.48 CFU/ml respectively. The droplet size in the mist was smaller than 2 μl. Each of these values represents the upper limit of the test used. Similarly, an additional stainless steel coupon with *C. difficile* was misted with water and treated with indirect plasma for 3 minutes, which resulted in a log reduction of 4.18 CFU/ml, for 1 minute which resulted in a 3.33 log reduction and for 3 minutes resulting in a 2.48 log reduction. Thus, misting the spores with fluid and then treating with plasma or indirect plasma resulted in significant killing or deactivating of the *C. difficile* spores.

In another experiment, a microscope glass slide with *C. difficile* was misted with water and treated with direct plasma for 3 minutes, which resulted in a log reduction of 4.00 CFU/ml. Thus, misting the spores on glass with fluid and then treating with plasma or indirect plasma resulted in a significant killing or deactivating of the *C. difficile* spores.

| Plasma Type | Treatment Time | Fluid Mist | Log Reduction (CFU/ml) | Surface |
|---|---|---|---|---|
| Direct | 30 sec | Yes | 3.43** | Stainless Steel |
| Direct | 1 min | Yes | 4.48** | Stainless Steel |
| Direct | 3 min | Yes | 4.48** | Stainless Steel |
| Indirect | 3 min | Yes | 4.18** | Stainless Steel |
| Indirect | 1 min | Yes | 3.33 | Stainless Steel |
| Indirect | 3 min | Yes | 2.48 | Stainless Steel |
| Direct | 1 min | Yes | 3.06 | Glass |
| Direct | 3 min | Yes | 4.00** | Glass |

**Denotes Upper limit of the measurement scale for the test results.

In another experiment as indicated in the chart below, a stainless steel coupon with *C. difficile* was treated for 1 minute with direct plasma and then treated for 4 minutes with an alcohol based sanitizer (which alone has little to no log reduction in *C. difficile*) and the result was a 2.71 CFU/ml log reduction in *C. difficile* spores. Thus, pre-treating spores with plasma and then with a applying an antimicrobial to the spores results in a significant kill or deactivation of the spores.

| Plasma Type | Treatment Time | Alcohol applied to Spores | Log Reduction (CFU/ml) | Surface |
|---|---|---|---|---|
| Direct | 1 min | Yes | 2.71 | Stainless Steel |

While the present invention has been illustrated by the description of embodiments thereof and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and/or illustrative examples shown and described. Accordingly, departures may be made from such details without departing from the spirit or scope of the applicants' general inventive concept.

We claim:

1. A method of killing or deactivating a spore comprising:
   applying a fluid to a dry spore surface containing one or more spores and
   applying direct plasma to the surface for a period of time.
2. The method of claim 1 wherein the fluid comprises water.
3. The method of claim 2 further comprising an additive in the water.
4. The method of claim 1 wherein the spore is *Clostridium difficile*.
5. The method of claim 1 wherein the spore is *Bacillus anthracis*.
6. The method of claim 1 wherein the fluid is in the form of a mist.
7. The method of claim 1 wherein the mist comprises droplets having a volume of between about 0.1 microliter and 500 microliters.
8. The method of claim 1 wherein the mist comprises droplets having a volume of less than about 250 microliters.
9. The method of claim 1 wherein the mist comprises droplets having a volume of less than about 100 microliters.
10. The method of claim 1 wherein the fluid is in the form of a vapor.
11. The method of claim 1 wherein the treatment time is less than about 3 minutes.
12. The method of claim 1 wherein the treatment time is less than about 1 minutes.
13. The method of claim 1 wherein the treatment time is less than about 30 seconds.
14. The method of claim 1 further comprising creating peroxynitrite in the fluid.
15. A method of killing or deactivating a spore comprising:
    applying a fluid to a dry surface containing one or more spores; and
    applying indirect plasma to the surface for a period of time.
16. The method of claim 15 wherein the fluid comprises water.
17. The method of claim 16 further comprising an additive in the water.
18. The method of claim 15 wherein the spore is *Clostridium difficile*.
19. The method of claim 15 wherein the spore is *Bacillus anthracis*.
20. The method of claim 15 wherein the fluid is in the form of a mist.
21. The method of claim 20 wherein the mist comprises droplets having a volume of between about 0.1 microliter and 500 microliters.
22. The method of claim 20 wherein the mist comprises droplets having a volume of less than about 250 microliters.
23. The method of claim 20 wherein the mist comprises droplets having a volume of less than about 100 microliters.
24. The method of claim 15 wherein the fluid is in the form of a vapor.
25. The method of claim 15 further comprising creating peroxynitrite in the fluid.
26. A method of killing or deactivating a spore comprising:
    treating a surface containing one or more spores with direct plasma or an indirect plasma for a period of time;
    applying an antimicrobial to the surface, wherein the surface contains one or more spores.
27. The method of claim 26 wherein the antimicrobial is an alcohol.
28. The method of claim 26 wherein the antimicrobial is a bleach based sanitizer.
29. The method of claim 26 wherein the antimicrobial is an alcohol based sanitizer.
30. The method of claim 26 wherein the antimicrobial is applied prior to treating the surface.

* * * * *